(12) United States Patent
Inberg

(10) Patent No.: US 6,912,050 B2
(45) Date of Patent: Jun. 28, 2005

(54) PHASE SHIFT MEASUREMENT FOR LUMINESCENT LIGHT

(75) Inventor: Steven Bradley Inberg, Fort Collins, CO (US)

(73) Assignee: Hach Company, Loveland, CO (US)

( * ) Notice: Subject to any disclaimer, the term of this patent is extended or adjusted under 35 U.S.C. 154(b) by 341 days.

(21) Appl. No.: 10/356,878

(22) Filed: Feb. 3, 2003

(65) Prior Publication Data

US 2004/0150819 A1 Aug. 5, 2004

(51) Int. Cl.[7] ............... G01J 3/30; G01N 21/64; G01N 21/75
(52) U.S. Cl. ............ 356/317; 250/458.1; 436/172
(58) Field of Search ................. 356/317, 318, 356/417; 250/458.1, 459.1, 461.1, 461.2; 436/172

(56) References Cited

U.S. PATENT DOCUMENTS

| | | | |
|---|---|---|---|
| 5,030,420 A | 7/1991 | Bacon et al. | |
| 5,194,913 A | 3/1993 | Myrick et al. | |
| 5,211,165 A | 5/1993 | Dumoulin et al. | |
| 5,462,879 A | 10/1995 | Bentsen | |
| 5,660,185 A | 8/1997 | Shmulewitz et al. | |
| 5,715,822 A | 2/1998 | Watkins et al. | |
| 5,818,582 A | * 10/1998 | Fernandez et al. | ........ 356/318 |
| 5,833,627 A | 11/1998 | Shmulewitz et al. | |
| 6,157,037 A | 12/2000 | Danielson | |
| 6,174,291 B1 | 1/2001 | McMahon et al. | |
| 6,185,445 B1 | 2/2001 | Knuttel | |
| 6,198,531 B1 | 3/2001 | Myrick et al. | |
| 6,270,464 B1 | 8/2001 | Fulton, III et al. | |
| 6,470,204 B1 | 10/2002 | Uzgiris et al. | |
| 6,487,434 B1 | 11/2002 | Kaiser et al. | |
| 6,529,276 B1 | 3/2003 | Myrick | |
| 6,529,764 B1 | 3/2003 | Kato et al. | |
| 6,567,687 B2 | 5/2003 | Front et al. | |
| 6,626,849 B2 | 9/2003 | Huitema et al. | |
| 6,675,037 B1 | 1/2004 | Tsekos | |
| 6,815,211 B1 | * 11/2004 | Blazewicz et al. | ........ 436/172 |
| 2001/0039378 A1 | 11/2001 | Lampman et al. | |
| 2003/0083572 A1 | 5/2003 | Satragano et al. | |

FOREIGN PATENT DOCUMENTS

EP 0 294 938 A2 12/1988
WO WO 03/019179 A1 3/2003

* cited by examiner

*Primary Examiner*—F. L. Evans
(74) *Attorney, Agent, or Firm*—Setter Ollila LLC

(57) ABSTRACT

A phase shift measurement system comprises an excitation system, a luminescent material, and a detection system. The excitation system transfers an excitation light wave. The luminescent material transfers a luminescent light wave in response to the excitation light wave. The detection system detects the luminescent light wave and generates a corresponding luminescent signal. The detection system processes the corresponding luminescent signal with DFT logic to determine a phase shift between the excitation light wave and the luminescent light wave.

50 Claims, 3 Drawing Sheets

PHASE SHIFT MEASUREMENT FOR LUMINESCENT LIGHT

BACKGROUND OF THE INVENTION

1. Field of the Invention

The invention is related to the field of luminescence, and in particular, to phase shift measurement between an excitation light wave and a luminescent light wave.

2. Statement of the Problem

The concentration of oxygen in water is measured with a probe. The oxygen in the water interacts with a luminescent material on the outside of the probe. This interaction between the oxygen and the luminescent material results in a phenomenon known as luminescent quenching. Thus, the amount of luminescent quenching indicates the concentration of oxygen in the water.

In operation, the probe directs excitation light of one wavelength to the luminescent material. The excitation light causes the luminescent material to generate luminescent light at a different wavelength. Luminescence quenching affects the amount of time that the luminescent material continues to luminescence light. Thus, if the excitation light signal's intensity varies sinusoidally, the luminescence quenching affects the phase shift between the excitation light and the luminescent light. The probe measures the phase shift between the excitation light and the luminescent light to assess the amount of luminescent quenching. As a result, the probe processes the phase shift to determine the concentration of oxygen in the water.

Existing technology probes use a servo feedback loop to measure the phase shift between the excitation light and the luminescent light. In some cases, the servo feedback loop introduces additional phase shift until the excitation light and the luminescent light are in phase, and the amount of additional phase shift should match the phase shift between the excitation light and the luminescent light. In other cases, the servo feedback loop introduces additional phase shift until the servo system detects that the excitation light and the luminescent light are 90 degrees out of phase. The additional phase shift is subtracted from 90 degrees to obtain the phase shift between the excitation light and the luminescent light.

The luminescent material must remain exposed to the excitation light until the servo system settles, and the servo settling time may take several seconds. Unfortunately, exposure of the luminescent material to the excitation light may degrade the luminescent material. In addition, the components of the probe introduce unwanted phase shift that is incorrectly attributed to the oxygen in the water. This unwanted phase shift adds error to the oxygen concentrations that are determined by the probe.

SUMMARY OF THE SOLUTION

The invention helps solve the above problems with technology to measure phase shift between excitation light and luminescent light. Advantageously, the technology may allow the duration of the excitation light to be significantly reduced to extend the useful life of the luminescent material. In addition, the technology may remove unwanted phase shift that is not attributable to luminescent quenching to improve the accuracy of the phase shift measurement. Examples of the invention include phase shift measurement systems, methods of phase shift measurement system operation, processing systems for phase shift measurement systems, methods of processing system operation, and products that direct processing system operation.

Some examples of the invention include a phase shift measurement system for luminescent light. The phase shift measurement system comprises: an excitation system, a luminescent material, and a detection system. The excitation system is configured to transfer a first excitation light wave. The luminescent material is configured to transfer a first luminescent light wave in response to the first excitation light wave. The detection system is configured to detect the first luminescent light wave and generate a corresponding first luminescent signal. The detection system is configured to process the corresponding first luminescent signal with Discrete Fourier Transform (DFT) logic to determine a first phase shift between the first excitation light wave and the first luminescent light wave.

In some variations, the detection system is configured to process the first phase shift to determine luminescent quenching.

In some variations, the detection system is configured to process the first phase shift to determine a concentration of an analyte in a liquid or a gas.

In some variations, the detection system is configured to process the first phase shift to determine a concentration of oxygen in water.

In some variations, the detection system is configured to adjust the first phase shift to remove unwanted phase shift introduced by the excitation system and the detection system.

In some variations, the excitation system is configured to transfer a second excitation light wave. The luminescent material is configured to transfer a reflected light wave in response to the second excitation light wave. The detection system is configured to detect the reflected light wave and generate a corresponding reflected signal. The detection system is configured to process the corresponding reflected signal with the DFT logic to determine a second phase shift between the second excitation light wave and the reflected light wave. The detection system is configured to adjust the first phase shift based on the second phase shift to remove unwanted phase shift introduced by the excitation system and the detection system.

In some variations, the corresponding first luminescent signal comprises a set of sample values of the first luminescent light wave and the DFT logic is configured to use a single frequency index to determine the first phase shift wherein the single frequency index comprises the number of cycles of the first excitation light wave needed to obtain the set of sample values for the DFT calculation interval.

In some variations, the first excitation light wave varies sinusoidally at a first reference frequency and the DFT logic is configured to perform frequency domain analysis on the corresponding first luminescent signal only at the first reference frequency.

In some variations, the first excitation light wave varies sinusoidally at a first reference frequency and at a second reference frequency. The first phase shift is between the first excitation light wave at the first reference frequency and the first luminescent light wave. The detection system is configured to process the corresponding first luminescent signal with the DFT logic to determine a second phase shift between the first excitation light wave at the second reference frequency and the first luminescent light wave.

In some variations, the first excitation light wave has a duration of less than 50 milliseconds.

Some examples of the invention include a processing system for phase shift measurement of luminescent light. In these examples, a light source system is configured to transfer a first excitation light wave to a luminescent material in response to an excitation signal, the luminescent material is configured to transfer a first luminescent light wave in response to the first excitation light wave, and a light detection system is configured to detect the first luminescent light wave and generate a corresponding first luminescent signal. The processing system comprises drive circuitry and response circuitry. The drive circuitry is configured to generate the excitation signal for the light source system. The response circuitry is configured to process the corresponding first luminescent signal from the light detection system with DFT logic to determine a first phase shift between the first excitation light wave and the first luminescent light wave.

Some examples of the invention include a product for phase shift measurement of luminescent light. In these examples, a light source system is configured to transfer a first excitation light wave to a luminescent material in response to an excitation signal, the luminescent material is configured to transfer a first luminescent light wave in response to the first excitation light wave, and a light detection system is configured to detect the first luminescent light wave and generate a corresponding first luminescent signal. The product comprises instructions and a memory that stores the instructions. The instructions are configured to direct a processing system to generate the excitation signal for the light source system and to process the corresponding first luminescent signal from the light detection system with DFT logic to determine a first phase shift between the first excitation light wave and the first luminescent light wave.

DESCRIPTION OF THE DRAWINGS

The same reference number represents the same element on all drawings.

DETAILED DESCRIPTION OF THE INVENTION

Figure 1:
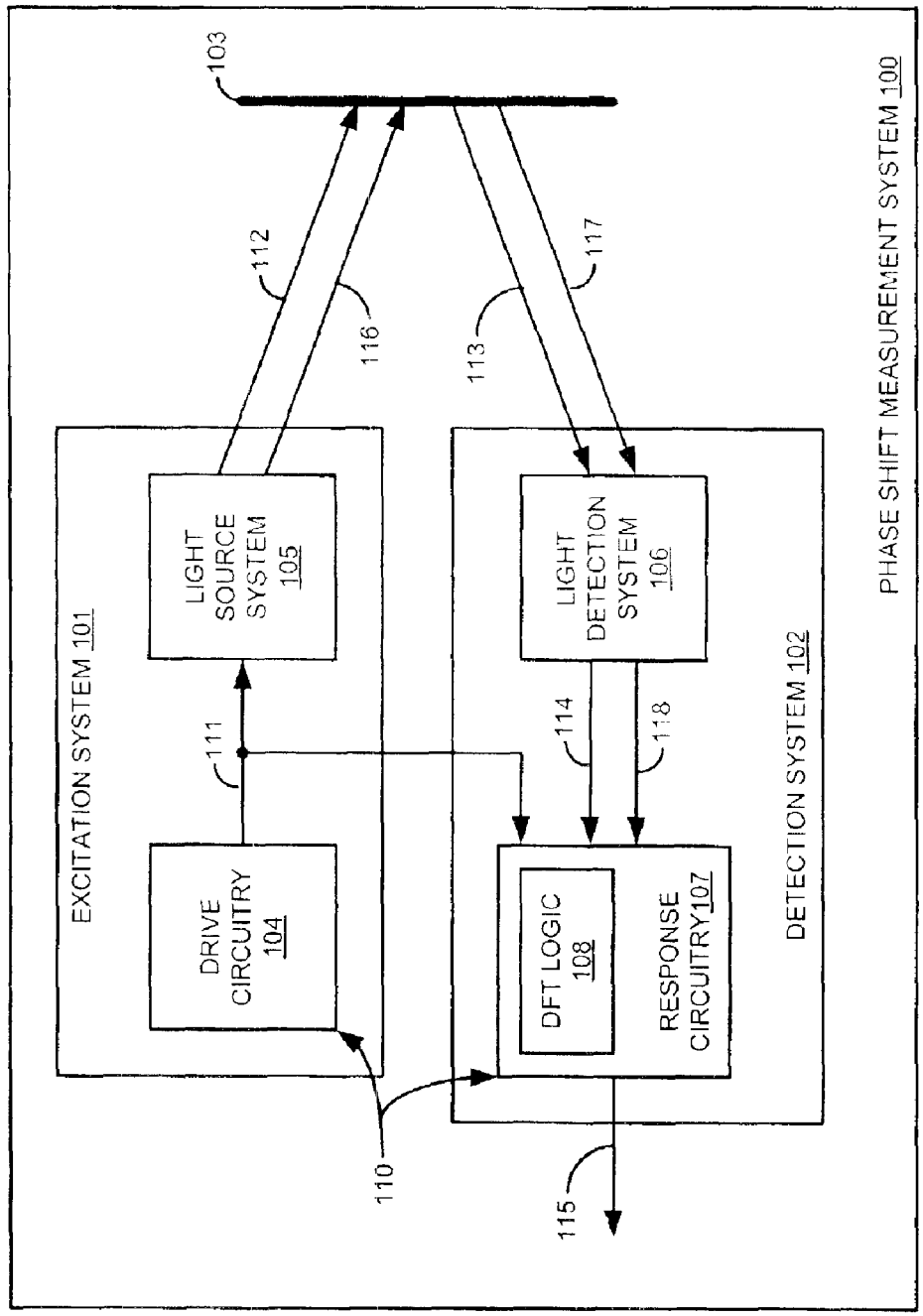
FIG. 1 illustrates a phase shift measurement system in an example of the invention.
Figure 2:
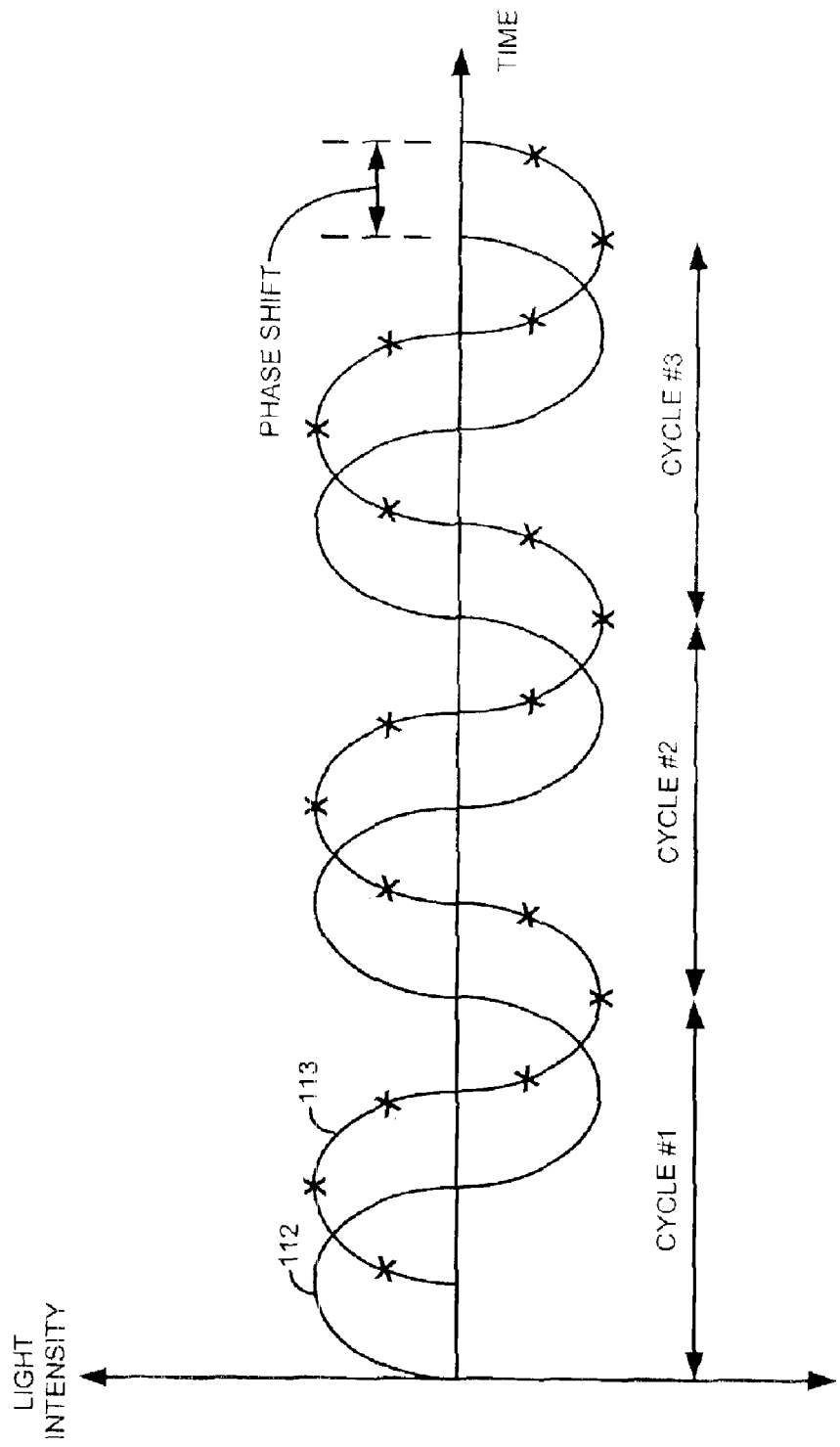
FIG. 2 illustrates light waves for a phase shift measurement system in an example of the invention.
Figure 3:
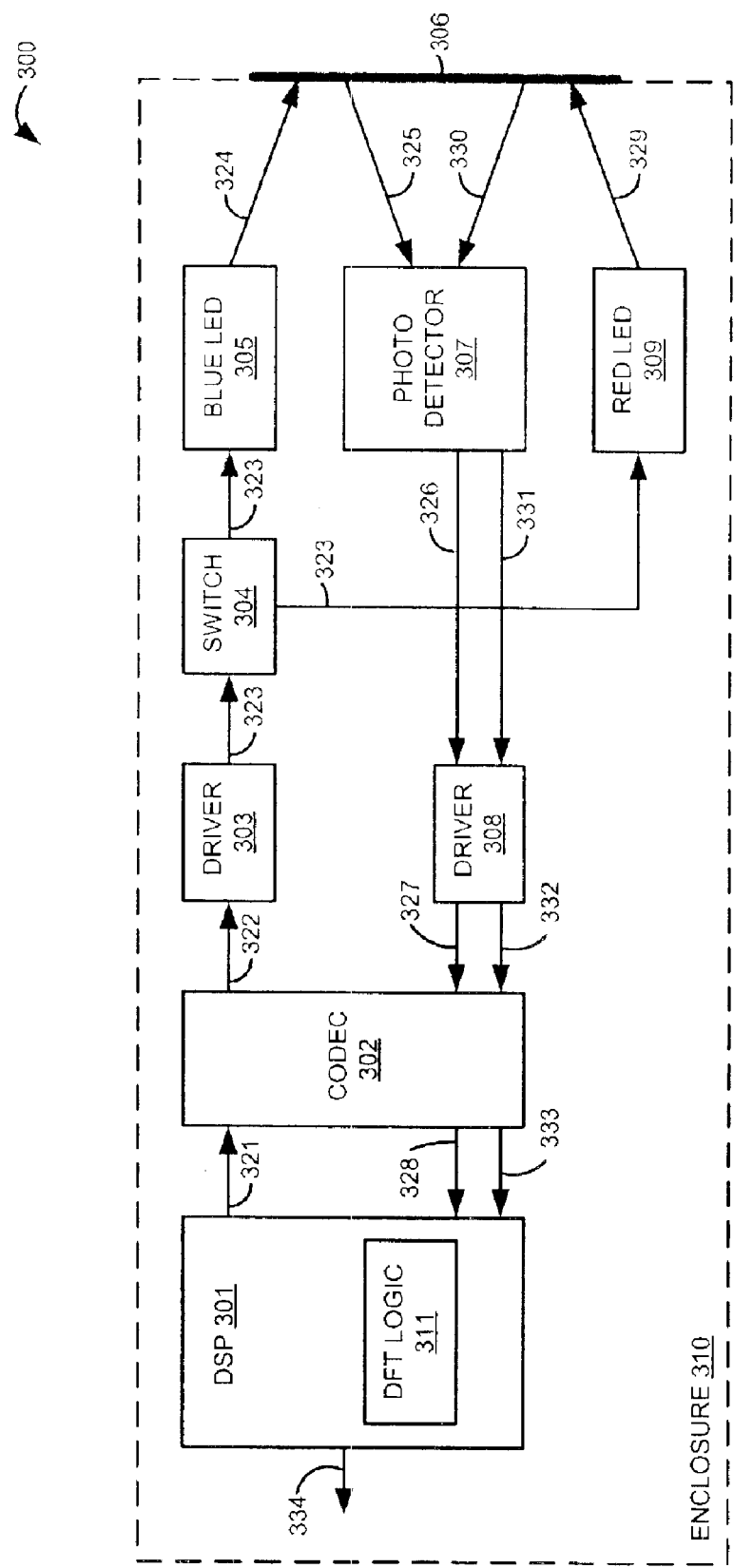
FIG. 3 illustrates a phase shift measurement system in an example of the invention.

FIGS. 1–3 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

EXAMPLE #1

FIG. 1 illustrates phase shift measurement system 100 in an example of the invention. Phase shift measurement system 100 comprises excitation system 101, detection system 102, and luminescent material 103. Excitation system 101 includes drive circuitry 104 and light source system 105. Detection system 102 includes light detection system 106 and response circuitry 107. Response circuitry 107 includes Discrete Fourier Transform (DFT) logic 108. The term "logic" is used in a general sense to indicate any type of hardware and programming that is used to perform DFT calculations. Together, drive circuitry 104 and response circuitry 107 comprise processing system 110. Based on this disclosure, those skilled in the art will appreciate how to modify and combine existing components to make phase shift measurement system 100.

In operation, drive circuitry 104 generates excitation signal 111 for light source system 105 and response circuitry 107. Light source system 105 transfers excitation light wave 112 to luminescent material 103 in response to excitation signal 111. Luminescent material 103 transfers luminescent light wave 113 in response to excitation light wave 112. Light detection system 106 detects luminescent light wave 113 and generates corresponding luminescent signal 114. Response circuitry 107 processes excitation signal 111 and luminescent signal 114 with DFT logic 108. DFT logic 108 determines the phase shift between excitation light wave 112 and luminescent light wave 113.

Advantageously, DFT logic 108 may determine the phase shift with much less exposure to excitation light than prior systems. For example, excitation light wave 112 may have duration of less than 0.05 seconds where prior systems required excitation light for at least 0.5 seconds. This relatively large reduction in excitation light over prior systems significantly lengthens the useful life of luminescent material 103.

Response circuitry 107 generates output signal 115, and in some variations, output signal 105 indicates the phase shift. In some variations, response circuitry 108 processes the phase shift to determine luminescent quenching, and output signal 105 indicates the luminescent quenching. In some variations, response circuitry 107 processes the phase shift to determine a concentration of an analyte in a liquid or a gas, and output signal 115 indicates the concentration. For example, response circuitry 107 may process the phase shift to determine a concentration of oxygen in water. In additional examples, response circuitry 107 may process the phase shift to determine a pH or a concentration of carbon dioxide, ammonia, or metal in water or gas based on the interactions of these species with the luminescent material.

In some variations, response circuitry 107 adjusts the phase shift to remove unwanted phase shift introduced by excitation system 101 and detection system 102. Advantageously, this adjustment helps isolate the phase shift of interest which is introduced by luminescent material 103. The adjustment may be accomplished as follows.

Drive circuitry 104 generates excitation signal 111 for light source system 105 and response circuitry 107. Light source system 105 transfers excitation light wave 116 to luminescent material 103 in response to excitation signal 111. Luminescent material 103 transfers reflected light wave 117 in response to excitation light wave 116. Importantly, luminescent material 103 does not introduce significant phase shift between excitation light wave 116 and reflected light wave 117. Light detection system 106 detects reflected light wave 117 and generates corresponding reflected signal 118. Response circuitry 107 processes excitation signal 111 and reflected signal 118 with DFT logic 108. DFT logic 108 determines a second phase shift between excitation light wave 116 and reflected light wave 117. Since luminescent material 103 does not introduce significant phase shift into the second phase shift determination, the second phase shift represents unwanted phase shift introduced by excitation system 101 and detection system 102. Response circuitry 107 adjusts the originally-determined phase shift based on the second phase shift to remove the unwanted phase shift.

FIG. 2 illustrates light waves 112–113 in an example of the invention. On FIG. 2, light waves 112–113 are plotted against a vertical intensity axis and a horizontal time axis. Note that FIG. 2 is highly simplified for illustrative purposes, and the actual parameters of light waves 112–113 may differ in some variations. For example, sine waves are shown, but the intensity of light waves 112–113 could vary according to cosine waves.

The intensity of excitation light wave 112 varies sinusoidally at a first reference frequency. Although shifted in phase, the intensity of luminescent light wave 113 also varies sinusoidally at the first reference frequency. Light detection system 106 samples luminescent light wave 113 to generate luminescent signal 114. The resulting set of samples are represented on FIG. 2 by the "X" markings luminescent light wave 113.

DFT logic 108 uses a single frequency index when processing the set of samples to determine the phase shift. This single frequency index comprises a number of cycles of excitation light wave 112 that are needed to obtain the set of sample values. In this simplified example, there are 18 samples in the set, and the number of cycles of excitation light wave 112 that are needed to obtain this set is three. Thus, the single frequency index would be three in this simplified example. The use of the single frequency index in this manner means that DFT logic 108 performs frequency domain analysis on luminescent signal 114 only at the first reference frequency.

In some variations, excitation light wave 112 is a multi-frequency signal. Thus, the intensity of excitation light wave 112 would vary sinusoidally at the first reference frequency and also at a second reference frequency. Response circuitry 107 could then process luminescent signal 114 with DFT logic 108 to determine a first phase shift between luminescent light wave 113 and excitation light wave 112 at the first reference frequency. Response circuitry 107 could also process luminescent signal 114 with DFT logic 108 to determine a second phase shift between luminescent light wave 113 and excitation light wave 112 at the second reference frequency. Note that a different frequency index would be used in the above two phase shift calculations because of the different references frequencies, but only a single frequency index would be used for each calculation.

Processing system 110 could be comprised of a digital signal processor, application specific integrated circuitry, logic circuitry, general-purpose microprocessor, or some other processing device. In some variations, processing system 110 executes instructions that direct processing system 110 to operate as described above. The instructions could comprise software, firmware, programmed integrated circuitry, or some other form of machine-readable instructions. Thus, a product may be comprised of a memory that stores the instructions. The memory may be internal or external to phase shift measurement system 100, and the memory could be comprised of a disk, tape, integrated circuit, server, or some other memory device.

EXAMPLE #2

FIG. 3 illustrates phase shift measurement system 300 in an example of the invention. Phase shift measurement system 300 is comprised of: Digital Signal Processor (DSP) 301, Coder/Decoder (Codec) 302, driver 303, switch 304, blue Light Emitting Diode (LED) 305, luminescent material 306, photo detector 307, driver 308, red LED 309, and enclosure 310. DSP 301 includes DFT logic 311. The term "logic" is used in a general sense to indicate any type of hardware and programming that is used to perform DFT calculations.

Enclosure 310 is a water proof plastic case that contains components 301–305 and 307–309. Luminescent material 306, such as a luminescent paint, is applied to the outside of enclosure 310. The portion of enclosure 310 where luminescent material 306 is applied is clear to allow light waves 324–325 and 329–330 to pass between luminescent material 306 and internal components 305, 307, and 309.

To measure the concentration of oxygen in water, the portion of enclosure 310 with luminescent material 306 is placed in the water. DSP 301 generates and transfers digital excitation signal 321. Codec 302 receives digital excitation signal 321, converts digital excitation signal 321 into corresponding analog excitation signal 322, and transfers analog excitation signal 322. Driver 303 receives analog excitation signal 322, converts analog excitation signal 322 from a voltage based signal to a current based signal to produce excitation signal 323, and transfers excitation signal 323. Switch 304 receives excitation signal 323 and switches excitation signal 323 on a path to blue LED 305. Blue LED 305 receives excitation signal 323, and in response, generates and transfers corresponding excitation light wave 324 toward luminescent material 306. The time duration of excitation light wave 324 should be a multiple of the period of the reference frequency for excitation light wave 324, and typically, multiple periods are used to average the effects of noise.

Oxygen in the water interacts with luminescent material 306 to affect the luminescence quenching of luminescent material 306. While in the water, luminescent material 306 receives excitation light wave 324, and in response, generates luminescent light wave 325. In this instance, the color of the luminescent light wave 325 is red. Luminescent material 306 introduces a phase shift, which is affected by luminescence quenching, between excitation light wave 324 and luminescent light wave 325. Thus, the phase shift indicates the amount of luminescence quenching, and the amount of luminescence quenching indicates the concentration of oxygen in the water.

Photo detector 307 receives luminescent light wave 325, converts luminescent light wave 325 into corresponding analog luminescent signal 326, and transfers analog luminescent signal 326. Driver 308 receives analog luminescent signal 326, converts analog luminescent signal 326 from a current based signal to a voltage based signal to produce luminescent signal 327, and transfers luminescent signal 327. Codec 302 receives luminescent signal 327, converts luminescent signal 327 into corresponding digital luminescent signal 328, and transfers digital luminescent signal 328. Digital luminescent signal 328 comprises a set of sample values for luminescent light wave 325. DFT logic 311 receives and processes the sample values of digital luminescent signal 328 according to the following Real Discrete Fourier Transform equations 1 and 2 to determine a phase shift using equation 3. Note, that the Real Discrete Fourier Transform is a real number simplification of the Complex Discrete Fourier Transform which deals with complex numbers. Note that the complex Discrete Fourier Transform could also have been used.

$$\mathrm{Re}X[k] = (2/N)\sum_{n=0}^{N-1} x[n]\cos(2\pi kn/N); \quad (1)$$

$$\mathrm{Im}X[k] = (-2/N)\sum_{n=0}^{N-1} x[n]\sin(2\pi kn/N); \text{ and} \quad (2)$$

$$\text{Phase shift} = \arctan(\mathrm{Im}\,X[k]/\mathrm{Re}\,X[k]); \text{ where} \quad (3)$$

N=the total number of sample values;
n=the number of the current sample value being processed;
x[n]=the current sample value being processed;
cos(2πkn/N)=the excitation signal; and
k=the frequency index=the number of complete cycles of the excitation light wave needed to obtain the N sample values from the luminescent light wave.

The following table indicates parameters for phase shift measurement system 300 in some variations.

| PARAMETER | VALUE |
| --- | --- |
| EXCITATION LIGHT WAVE REFERENCE FREQUENCY | 4069 Hz |
| EXCITATION LIGHT WAVE TIME DURATION | 17.4 MILLISECONDS |
| LUMINESCENT LIGHT WAVE SAMPLING FREQUENCY | 97656 Hz |
| TOTAL NUMBER OF SAMPLES (N) | 1704 |
| FREQUENCY INDEX (k) | 71 |

Unfortunately, components other than luminescent material 306 also introduce unwanted phase shift that adds error to the first phase shift because the unwanted phase shift is not related to the concentration of oxygen in the water. The amount of unwanted phase shift introduced by these other components tends to vary with temperature. The amount of unwanted phase shift may be periodically determined and subtracted from the first phase shift to obtain a corrected phase shift that is attributed to the luminescent quenching of the oxygen in the water.

To remove the unwanted phase shift, DSP 301 generates and transfers digital excitation signal 321. Codec 302 receives digital excitation signal 321, converts digital excitation signal 321 into corresponding analog excitation signal 322, and transfers analog excitation signal 322. Driver 303 receives analog excitation signal 322, converts analog excitation signal 322 from a voltage based signal to a current based signal to produce excitation signal 323, and transfers excitation signal 323. Switch 304 receives excitation signal 323, but this time, switch 304 switches excitation signal 323 on a path to red LED 309. Red LED 309 receives excitation signal 323, and in response, generates and transfers corresponding excitation light wave 329 toward luminescent material 306. The time duration of excitation light wave 329 should be a multiple of the period of the reference frequency for excitation light wave 329, and typically, multiple periods are used to average the effects of noise.

Luminescent material 306 receives excitation light wave 329, and in response, reflects reflected light wave 330. Luminescent material 306 does not introduce a phase shift between excitation light wave 329 and reflected light wave 330. Thus, any phase shift between excitation light wave 329 and reflected light wave 330 is introduced by components other than luminescent material 306. Note that luminescent light wave 325 and reflected light wave 330 would both be red. Note that reflections of excitation light wave 324 would be blue. Note that no phase shifted red luminescent light waves are generated in response to red excitation light wave 329, only red reflected light is transferred with no phase shift. A filter that passes only red light is used between luminescent material 306 and photo detector 307. The filter passes red luminescent light wave 325 and red reflected light wave 330. The filter blocks reflections of blue excitation light wave 324.

Photo detector 307 receives reflected light wave 330, converts reflected light wave 330 into corresponding analog reflected signal 331, and transfers analog reflected signal 331. Driver 308 receives analog reflected signal 331, converts analog reflected signal 331 from a current based signal to a voltage based signal to produce reflected signal 332, and transfers reflected signal 332. Codec 302 receives reflected signal 332, converts reflected signal 332 into corresponding digital reflected signal 333, and transfers digital reflected signal 333. Digital reflected signal 333 comprises a set of sample values for reflected light wave 330.

DFT logic 311 receives and processes the sample values of digital reflected signal 333 according to equations 1–3 to determine a second phase shift that is attributable to the components in system 300 other than luminescent material 306. DSP 301 subtracts the second phase shift from the first phase shift to obtain a corrected phase shift. DSP 301 processes the corrected phase shift to determine the amount of luminescent quenching. DSP 301 processes the amount of luminescent quenching to determine the concentration of oxygen in the water. DSP 301 transfers output signal 334 indicating the concentration of oxygen in the water.

In some variations, excitation light wave 324 is a multi-frequency signal. Thus, the intensity of excitation light wave 324 would vary sinusoidally at a first reference frequency and at a second reference frequency. DSP 301 could process digital luminescent signal 328 with DFT logic 311 to determine a first phase shift between excitation light wave 324 at the first reference frequency and luminescent light wave 325. DSP 301 could also process digital luminescent signal 328 with DFT logic 311 to determine a second phase shift between excitation light wave 324 at the second reference frequency and luminescent light wave 325. Note that a different frequency index would be used in the above two phase shift calculations because of the different reference frequencies.

In some variations, DSP 301 executes instructions that direct DSP 301 to operate as described above. The instructions could comprise software, firmware, programmed integrated circuitry, or some other form of machine-readable instructions. Thus, a product may be comprised of a memory that stores the instructions. The memory may be internal or external to phase shift measurement system 300, and the memory could be comprised of a disk, tape, integrated circuit, server, or some other memory device.

Example #1 and Example #2 can be correlated as follows. Luminescent material 103 corresponds to luminescent material 306. Drive circuitry 104 corresponds to DSP 301. Light source system 105 corresponds to components 302–305 and 309. Light detection system 106 corresponds to components 307, 308, and 302. Response circuitry 107 and DFT logic 108 correspond to DSP 301 and DFT logic 311.

What is claimed is:
1. A phase shift measurement system for luminescent light, the phase shift measurement system comprising:
an excitation system configured to transfer a first excitation light wave;
a luminescent material configured to transfer a first luminescent light wave in response to the first excitation light wave; and a detection system configured to detect the first luminescent light wave and generate a corresponding first luminescent signal, process the corresponding first luminescent signal with Real or Complex Discrete Fourier Transform (DFT) logic to determine a first phase shift between the first excitation light wave and the first luminescent light wave.

2. The phase shift measurement system of claim 1 wherein the detection system is configured to process the first phase shift to determine luminescent quenching.

3. The phase shift measurement system of claim 1 wherein the detection system is configured to process the first phase shift to determine a concentration of an analyte in a liquid or a gas.

4. The phase shift measurement system of claim 1 wherein the detection system is configured to process the first phase shift to determine a concentration of oxygen in water.

5. The phase shift measurement system of claim 1 wherein the detection system is configured to adjust the first phase shift to remove unwanted phase shift introduced by the excitation system and the detection system.

6. The phase shift measurement system of claim 1 wherein:
the excitation system is configured to transfer a second excitation light wave;
the luminescent material is configured to transfer a reflected light wave in response to the second excitation light wave; and
the detection system is configured to detect the reflected light wave and generate a corresponding reflected signal, process the corresponding reflected signal with the DFT logic to determine a second phase shift between the second excitation light wave and the reflected light wave, and to adjust the first phase shift based on the second phase shift to remove unwanted phase shift introduced by the excitation system and the detection system.

7. The phase shift measurement system of claim 1 wherein the corresponding first luminescent signal comprises a set of sample values of the first luminescent light wave and the DFT logic is configured to use a single frequency index to determine the first phase shift wherein the single frequency index comprises a number of cycles of the first excitation light wave needed to obtain the set of sample values.

8. The phase shift measurement system of claim 1 wherein the first excitation light wave varies sinusoidally at a first reference frequency and the DFT logic is configured to perform frequency domain analysis on the corresponding first luminescent signal only at the first reference frequency.

9. The phase shift measurement system of claim 1 wherein the first excitation light wave varies sinusoidally at a first reference frequency and at a second reference frequency, the first phase shift is between the first excitation light wave at the first reference frequency and the first luminescent light wave, and the detection system is configured to process the corresponding first luminescent signal with the DFT logic to determine a second phase shift between the first excitation light wave at the second reference frequency and the first luminescent light wave.

10. The phase shift measurement system of claim 1 wherein the first excitation light wave has a duration of less than 50 milliseconds.

11. A method of operating a phase shift measurement system for luminescent light, the method comprising:
transferring a first excitation light wave to a luminescent material;
transferring a first luminescent light wave from the luminescent material in response to the first excitation light wave;
detecting the first luminescent light wave and generating a corresponding first luminescent signal; and
processing the corresponding first luminescent signal with Real or Complex Discrete Fourier Transform (DFT) logic to determine a first phase shift between the first excitation light wave and the first luminescent light wave.

12. The method of claim 11 further comprising processing the first phase shift to determine luminescent quenching.

13. The method of claim 11 further comprising processing the first phase shift to determine a concentration of an analyte in a liquid or a gas.

14. The method of claim 11 further comprising processing the first phase shift to determine a concentration of oxygen in water.

15. The method of claim 11 further comprising adjusting the first phase shift to remove unwanted phase shift introduced by components of the phase shift measurement system other than the luminescent material.

16. The method of claim 11 further comprising:
transferring a second excitation light wave to the luminescent material;
transferring a reflected light wave from the luminescent material in response to the second excitation light wave;
detecting the reflected light wave and generating a corresponding reflected signal;
processing the corresponding reflected signal with the DFT logic to determine a second phase shift between the second excitation light wave and the reflected light wave; and
adjusting the first phase shift based on the second phase shift to remove unwanted phase shift introduced by components of the phase shift measurement system other than the luminescent material.

17. The method of claim 11 wherein generating the corresponding first luminescent signal comprises generating a set of sample values of the first luminescent light wave, wherein processing the corresponding first luminescent signal with the DFT logic to determine the first phase shift comprises processing the set of sample values with the DFT logic using a single frequency index to determine the first phase shift, and wherein the single frequency index comprises a number of cycles of the first excitation light wave needed to obtain the set of sample values.

18. The method of claim 11 wherein the first excitation light wave varies sinusoidally at a first reference frequency and wherein processing the corresponding first luminescent signal with the DFT logic to determine the first phase shift comprises performing frequency domain analysis on the corresponding first luminescent signal only at the first reference frequency.

19. The method of claim 11 wherein the first excitation light wave varies sinusoidally at a first reference frequency and at a second reference frequency and wherein processing the corresponding first luminescent signal with the DFT logic to determine the first phase shift comprises determining the first phase shift between the first excitation light wave at the first reference frequency and the first luminescent light wave, and further comprising processing the corresponding first luminescent signal with the DFT logic to determine a second phase shift between the first excitation light wave at the second reference frequency and the first luminescent light wave.

20. The method of claim 11 wherein transferring the first excitation light wave to the luminescent material comprises transferring the first excitation light wave to the luminescent material for a duration of less than 50 milliseconds.

21. A processing system for phase shift measurement of luminescent light, wherein a light source system is configured to transfer a first excitation light wave to a luminescent material in response to an excitation signal, the luminescent material is configured to transfer a first luminescent light wave in response to the first excitation light wave, and a light detection system is configured to detect the first luminescent light wave and generate a corresponding first luminescent signal, the processing system comprising:

drive circuitry configured to generate the excitation signal for the light source system; and response circuitry configured to process the corresponding first luminescent signal from the light detection system with Real or Complex Discrete Fourier Transform (DFT) logic to determine a first phase shift between the first excitation light wave and the first luminescent light wave.

22. The processing system of claim 21 wherein the response circuitry is configured to process the first phase shift to determine luminescent quenching.

23. The processing system of claim 21 wherein the response circuitry is configured to process the first phase shift to determine a concentration of an analyte in a liquid or a gas.

24. The processing system of claim 21 wherein the response circuitry is configured to process the first phase shift to determine a concentration of oxygen in water.

25. The processing system of claim 21 wherein the response circuitry is configured to adjust the first phase shift to remove unwanted phase shift introduced by the drive circuitry, the light source system, the light detection system, and the response circuitry.

26. The processing system of claim 21 wherein the light source system is configured to transfer a second excitation light wave to the luminescent material in response to the excitation signal, the luminescent material is configured to transfer a reflected light wave in response to the second excitation light wave, the light detection system is configured to detect the reflected light wave and generate a corresponding reflected signal, and wherein:

the response circuitry is configured to process the corresponding reflected signal from the light detection system with the DFT logic to determine a second phase shift between the second excitation light wave and the reflected light wave and adjust the first phase shift based on the second phase shift to remove unwanted phase shift introduced by the drive circuitry, the light source system, the light detection system, and the response circuitry.

27. The processing system of claim 21 wherein the corresponding first luminescent signal comprises a set of sample values of the first luminescent light wave and the DFT logic is configured to use a single frequency index to determine the first phase shift wherein the single frequency index comprises a number of cycles of the first excitation light wave needed to obtain the set of sample values.

28. The processing system of claim 21 wherein the first excitation light wave varies sinusoidally at a first reference frequency and the DFT logic is configured to perform frequency domain analysis on the corresponding first luminescent signal only at the first reference frequency.

29. The processing system of claim 21 wherein the first excitation light wave varies sinusoidally at a first reference frequency and at a second reference frequency, the first phase shift is between the first excitation light wave at the first reference frequency and the first luminescent light wave, and the response circuitry is configured to process the corresponding first luminescent signal with the DFT logic to determine a second phase shift between the first excitation light wave at the second reference frequency and the first luminescent light wave.

30. The processing system of claim 21 wherein the first excitation light wave has a duration of less than 50 milliseconds.

31. A method of operating a processing system for phase shift measurement of luminescent light, wherein a light source system transfers a first excitation light wave to a luminescent material in response to an excitation signal, the luminescent material transfers a first luminescent light wave in response to the first excitation light wave, and a light detection system detects the first luminescent light wave and generates a corresponding first luminescent signal, the method comprising:

generating the excitation signal for the light source system; and processing the corresponding first luminescent signal from the light detection system with Real or Complex Discrete Fourier Transform (DFT) logic to determine a first phase shift between the first excitation light wave and the first luminescent light wave.

32. The method of claim 31 further comprising processing the first phase shift to determine luminescent quenching.

33. The method of claim 31 further comprising processing the first phase shift to determine a concentration of an analyte in a liquid or a gas.

34. The method of claim 31 further comprising processing the first phase shift to determine a concentration of oxygen in water.

35. The method of claim 31 further comprising adjusting the first phase shift to remove unwanted phase shift introduced by the processing system, the light source system, and the light detection system.

36. The method of claim 31 wherein the light source system transfers a second excitation light wave to the luminescent material in response to the excitation signal, the luminescent material transfers a reflected light wave in response to the second excitation light wave, the light detection system detects the reflected light wave and generates a corresponding reflected signal, and further comprising:

processing the corresponding reflected signal from the light detection system with the DFT logic to determine a second phase shift between the second excitation light wave and the reflected light wave; and adjusting the first phase shift based on the second phase shift to remove unwanted phase shift introduced by the processing system, the light source system, and the light detection system.

37. The method of claim 31 wherein the corresponding first luminescent signal comprises a set of sample values of the first luminescent light wave, wherein processing the corresponding first luminescent signal with the DFT logic to determine the first phase shift comprises processing the set of sample values with the DFT logic using a single frequency index to determine the first phase shift, and wherein the single frequency index comprises a number of cycles of the first excitation light wave needed to obtain the set of sample values.

38. The method of claim 31 wherein the first excitation light wave varies sinusoidally at a first reference frequency and wherein processing the corresponding first luminescent signal with the DFT logic to determine the first phase shift comprises performing frequency domain analysis on the corresponding first luminescent signal only at the first reference frequency.

39. The method of claim 31 wherein the first excitation light wave varies sinusoidally at a first reference frequency and at a second reference frequency, and wherein processing the corresponding first luminescent signal with the DFT logic to determine the first phase shift comprises determining the first phase shift between the first excitation light wave at the first reference frequency and the first luminescent light wave, and further comprising processing the corresponding first luminescent signal with the DFT logic to determine a second phase shift between the first excitation light wave at the second reference frequency and the first luminescent light wave.

40. The method of claim 31 wherein the first excitation light wave has a duration of less than 50 milliseconds.

41. A product for phase shift measurement of luminescent light, wherein a light source system is configured to transfer a first excitation light wave to a luminescent material in response to an excitation signal, the luminescent material is configured to transfer a first luminescent light wave in response to the first excitation light wave, and a light detection system is configured to detect the first luminescent light wave and generate a corresponding first luminescent signal, the product comprising:

instructions configured to direct a processing system to generate the excitation signal for the light source system and to process the corresponding first luminescent signal from the light detection system with Real or Complex Discrete Fourier Transform (DFT) logic to determine a first phase shift between the first excitation light wave and the first luminescent light wave; and a memory that stores the instructions.

42. The product of claim 41 wherein the instructions are configured to direct the processing system to process the first phase shift to determine luminescent quenching.

43. The product of claim 41 wherein the instructions are configured to direct the processing system to process the first phase shift to determine a concentration of an analyte in a liquid or a gas.

44. The product of claim 41 wherein the instructions are configured to direct the processing system to process the first phase shift to determine a concentration of oxygen in water.

45. The product of claim 41 wherein the instructions are configured to direct the processing system to adjust the first phase shift to remove unwanted phase shift introduced by the processing system, the light source system, and the light detection system.

46. The product of claim 41 wherein the light source system is configured to transfer a second excitation light wave to the luminescent material in response to the excitation signal, the luminescent material is configured to transfer a reflected light wave in response to the second excitation light wave, the light detection system is configured to detect the reflected light wave and generate a corresponding reflected signal, and wherein:

the instructions are configured to direct the processing system to process the corresponding reflected signal from the light detection system with the DFT logic to determine a second phase shift between the second excitation light wave and the reflected light wave and adjust the first phase shift based on the second phase shift to remove unwanted phase shift introduced by the processing system, the light source system, and the light detection system.

47. The product of claim 41 wherein the corresponding first luminescent signal comprises a set of sample values of the first luminescent light wave and wherein the DFT logic is configured to use a single frequency index to determine the first phase shift wherein the single frequency index comprises a number of cycles of the first excitation light wave needed to obtain the set of sample values.

48. The product of claim 41 wherein the first excitation light wave varies sinusoidally at a first reference frequency and the DFT logic is configured to perform frequency domain analysis on the corresponding first luminescent signal only at the first reference frequency.

49. The product of claim 41 wherein the first excitation light wave varies sinusoidally at a first reference frequency and at a second reference frequency, the first phase shift is between the first excitation light wave at the first reference frequency and the first luminescent light wave, and the instructions are configured to direct the processing system to process the corresponding first luminescent signal with the DFT logic to determine a second phase shift between the first excitation light wave at the second reference frequency and the first luminescent light wave.

50. The product of claim 41 wherein the first excitation light wave has a duration of less than 50 milliseconds.

* * * * *